United States Patent

Yamazaki et al.

Patent Number: 5,585,512
Date of Patent: Dec. 17, 1996

[54] ESTERS OF P-HYDROXYANILINE MUSTARD

[75] Inventors: Yoshimitsu Yamazaki; Yoshikatsu Ogawa; Hiroaki Okuno, all of Tsukuba, Japan

[73] Assignee: Director-General of Agency of Industrial Science and Technology, Tokyo, Japan

[21] Appl. No.: 394,814

[22] Filed: Feb. 27, 1995

[30]  Foreign Application Priority Data

May 20, 1994 [JP] Japan .................................. 6-131303

[51] Int. Cl.$^6$ ...................... C07C 261/00; C07C 269/00; C07C 69/76
[52] U.S. Cl. ............................. 560/31; 560/60; 560/110
[58] Field of Search .................. 560/31, 60, 110

[56]  References Cited

U.S. PATENT DOCUMENTS

| | | | |
|---|---|---|---|
| 3,592,949 | 7/1971 | Teach et al. | 560/31 |
| 3,670,010 | 6/1972 | Teach | 560/31 |
| 3,792,994 | 2/1974 | Baker et al. | 560/31 |
| 4,282,368 | 8/1981 | Merger et al. | 560/31 |

OTHER PUBLICATIONS

A Collection of the Substance of a Lecture, p. 36, vol. 4, Mar. 5, 1994.

*Primary Examiner*—James O. Wilson
*Attorney, Agent, or Firm*—Birch, Stewart, Kolasch & Birch, LLP

[57]  ABSTRACT

There is disclosed an ester compound that is resistant to decomposition in blood, but is quickly hydrolyzed in cancer cells, and functions as an anticancer agent. The ester compound has a structure represented by formula (I) or formula (II):

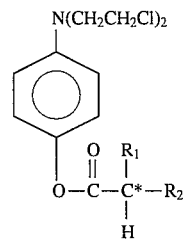

formula (I)

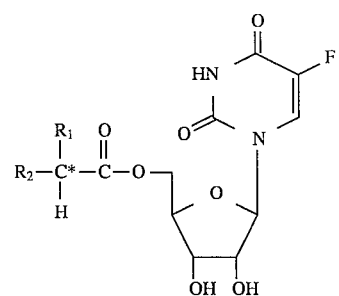

formula (II)

wherein $R_1$ represents a methyl group, a methoxy group, or a trifluoroacetamido group; $R_2$ represents a phenyl group or a phenylmethyl group; and the absolute configuration of the asymmetric center marked with an asterisk is $\underline{R}$.

5 Claims, No Drawings

ESTERS OF P-HYDROXYANILINE MUSTARD

FIELD OF THE INVENTION

The present invention relates to an ester-type anticancer agent that is hydrolyzed in cancer (malignancy) cells but resistant to decomposition in blood, and a method of producing the same.

BACKGROUND OF THE INVENTION

In the case of p-hydroxyaniline mustard (having the below-given formula IV) or 5-fluorouridine (having the below-given formula V), which are known to respectively have anticancer (antitumor) action, in order to mitigate the side effects of these compounds, the following method is attempted: their hydroxyl group is temporarily esterified, no render it inactive, so that when each of these compounds is administered into an organism, the compound is converted into the active form only in cancer cells by hydrolysis with esterases in the cancer cells (T. J. Bardos et al., Ann. N.Y. Acad. Sci., 163, 1006 (1969), and JP-A ("JP-A" means unexamined published Japanese patent application ) No. 91998/1982).

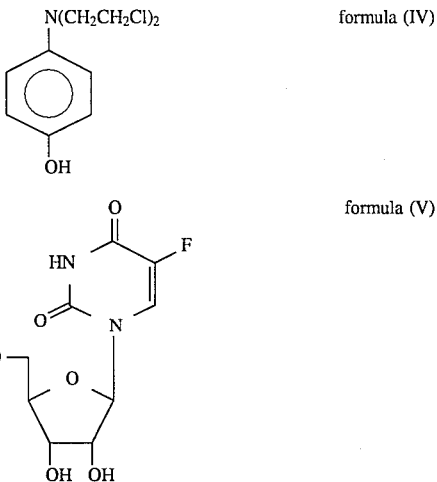

However, the ester compounds conventionally used cannot avoid the problem that most of the compound's acyl groups are hydrolyzed by the action of esterases existing in blood before the compounds reach cancer tissue.

SUMMARY OF THE INVENTION

An object of the present invention is to provide an ester compound that is hydrolyzed in cancer cells but is resistant to hydrolyzation in blood.

Another object of the present invention is to provide a method of producing the above ester compound.

Other and further objects, features, and advantages of the invention will appear more fully from the following description.

DETAILED DESCRIPTION OF THE INVENTION

The present inventors have studied variously the structures of esters that are hydrolyzed in cancer cells but that resist decomposition in blood. Then we have found that the stereostructure of an acyl group having an asymmetric carbon atom in the α-position affects greatly the hydrolyzability.

That is, the ester obtained by acylating p-hydroxyaniline mustard with a particular acyl group (in the racemic form) was treated with various cancer cells or whole blood of rats or humans, and the absolute configuration and the optical purity of the produced carboxylic acid was studied. As a result, it was found that hydrolysis with cancer cells generally produces a carboxylic acid with the absolute configuration $\underline{R}$ with high stereoselectivity. On the other hand, hydrolysis in blood is liable to preferentially produce the ($\underline{R}$)-carboxylic acid, with low stereoselectivity. Further, surprisingly, it was found than, for some acyl groups, the acyl group having the ($\underline{R}$) configuration is preferentially hydrolyzed by human leukemia cells U937, whereas the acyl group having the ($\underline{S}$) configuration is preferentially hydrolyzed in normal human whole blood. Therefore, the stereoselectivity in cancer and normal blood is thus reversed in some cases. Further, in the case of 5-fluorouridine ester, wherein the 5'-position is acylated with a particular acyl group (in the racemic form), it was found that the ester having the ($\underline{R}$)-acyl group is hydrolyzed stereoselectively in cancer cells, whereas the ester having the ($\underline{S}$) configuration is preferentially hydrolyzed in blood.

The present invention has been completed based on the above finding.

In the present invention, an anticancer compound having a hydroxyl group is acylated with an asymmetric acyl group having a stereostructure that is suitable for the stereoselectivity of esterases in cancer cells but is unsuitable for the stereoselectivity of esterases in blood or normal cells. As a result, the particular anticancer agent is temporarily made inactive. When this anticancer agent is administered into a living body (an organism), the acyl group is preferentially hydrolyzed in cancer cells, based on the stereoselectivity of the enzyme reaction, and it is removed, so that the activity of the anticancer agent is exhibited.

That is, the present invention provides:

(1) an ester compound having a structure represented by the formula (I):

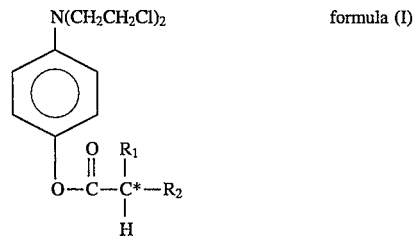

wherein $R_1$ represents a methyl group, a methoxy group, or a trifluoroacetamido group; $R_2$ represents a phenyl group or a phenylmethyl group; and the absolute configuration of the asymmetric center marked with an asterisk is R;

(2) an ester compound having a structure represented by the formula (II):

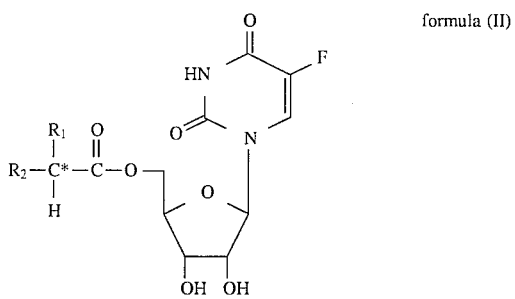

formula (II)

wherein $R_1$ represents a methyl group, a methoxy group, or a trifluoroacetamido group; $R_2$ represents a phenyl group or a phenylmethyl group; and the absolute configuration of the asymmetric center marked with an asterisk is R;

(3) a method of producing an ester of p-hydroxyaniline mustard that is improved in pharmacokinetics, comprising acylating the hydroxyl group in the p-position of a p-hydroxyaniline mustard with an acyl group represented by the formula (III), wherein the absolute configuration of the asymmetric center marked with an asterisk is R:

formula (III)

wherein $R_1$ represents a methyl group or a trifluoroacetamido group; $R_2$ represents a phenyl group or a phenylmethyl group; and the absolute configuration of the asymmetric center marked with an asterisk is R; and (4) a method of producing an ester of 5-fluorouridine or 5-fluorodeoxyuridine that is improved in pharmacokinetics, comprising acylating the hydroxyl group in the 5'-position of a 5-fluorouridine or a 5-fluorodeoxyuridine with an acyl group represented by the above-mentioned formula (III), wherein the absolute configuration of the asymmetric center marked with an asterisk is R.

The esters for anticancer agents of the present invention are novel compounds. The present invention led to the new finding that esterases in cancer cells and esterases in blood and other normal tissues have different stereoselectivities.

Now, preferred embodiments of the ester compound of the present invention and the method of producing it will be described.

In formula (I), (II), or (III), the case wherein $R_1$ is a methyl group and $R_2$ is a phenyl group; the case wherein $R_1$ is a methoxy group and $R_2$ is a phenyl group; and the case wherein $R_1$ is a trifluoroacetamido group and $R_2$ is a phenylmethyl group, are preferable. Preferable acyl groups out of those that are represented by formula (III) are represented by the following formulae (IIIa), (IIIb), and (IIIc):

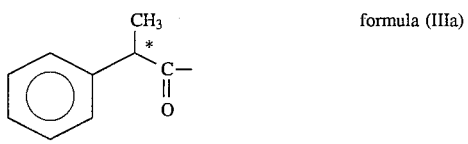

formula (IIIa)

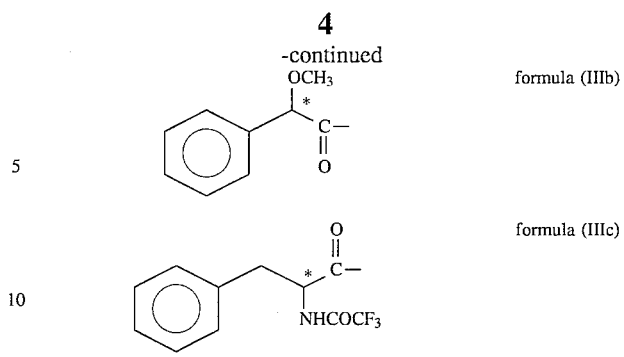

The ester for anticancer agent of the present invention can be obtained by activating the (R)-carboxylic acid corresponding to the acyl group represented by formula (III), preferably formula (IIIa), (IIIb), or (IIIc), by a known method, such as the acid chloride method, the DCC method, and the carbonyldiimidazole method; and coupling the (R)-carboxylic acid with p-hydroxyaniline mustard or 2',3'-isopropylidene-5-fluorouridine. In the latter case, the isopropylidene-protecting group is quickly eliminated with an acid treatment. Of the raw materials, p-hydroxyaniline mustard and (R)-N-trifluoroacetylphenylalanine can be easily synthesized by known methods (M. H. Benn et al., J. Chem. Soc., 2365 (1961); M. W. Holladay et al. J. Org. Chem., 3900 (1991)), and 2',3'-isopropylidene-5-fluorouridine is derived from commercially available 5-fluorouridine by a known method (K. A. Watanabe et al., J. Med. Chem., 24, 893 (1981)). (R)-2-phenylpropionic acid and (R)-2-methoxy-2-phenylacetic acid are commercially available. The amount of the (R)-carboxylic acid to be used for p-hydroxyaniline mustard or 2',3'-isopropylidene-5-fluorouridine may be stoichiometric.

The reaction conditions for the above coupling can be those that are employed in usual coupling, and the coupling reaction for the method of the present invention can be attained at a temperature from ordinary temperature to a temperature cooled with ice, in from several hours to around a day.

In the production of 5'-esterified 5-fluorodeoxyuridine, acylation of 5-fluorodeoxyuridine is carried out directly without first introducing an isopropylidene group. 3'-esterified 5-fluorodeoxyuridine, which occurs as a by-product of the 5'-ester, can be removed from the 5'-ester by means of column chromatography or the like.

The ester compound of the present invention represented by formula (I) or (II) is an ester functioning as an anticancer agent that is readily hydrolyzed in cancer cells but is relatively resistant to decomposition in blood. Further, in the case of rats, when the hydrolyzability of the above ester was tested using homogenates of normal rat liver, pancreas, and muscle, these tissues sometimes showed a stereoselectivity like blood, which is different from that of cancer cells. Therefore, if the stereostructure of the acyl group is suitably chosen, the ester compound of the present invention is useful as an ester-type anticancer agent that can attack cancer cells which avoiding damage to normal cells to the utmost.

Methods for administering and the dose of the ester compound to be administered as an anticancer agent of the present invention can be the same as those for conventional non-ester-type compounds.

The compound of the present invention is used as an ester-type anticancer agent that is resistant to decomposition in blood but is quickly hydrolyzed in cancer cells, to become active. According to the present invention, an anticancer agent can be esterified so that it may be activated by a hydrolysis reaction more readily in cancer cells than in blood or normal cells, and therefore the stability in blood is increased, the side effects on normal cells are reduced, and the selective attacking force on cancer cells can be increased.

Now, the present invention will be described in detail with reference to the following Synthetic Examples and Examples, but the present invention is not limited to them.

SYNTHETIC EXAMPLE 1

(Synthesis of (±)-4-bis(2-chloroethyl)aminophenyl 2-phenylpropionate (Ia))

Twenty mg of p-hydroxyaniline mustard was dissolved in a mixture of 200 µl of tetrahydrofuran and 100 µl of pyridine; then 100 µl of (±)-2-phenylpropionyl chloride was added thereto under cooling with ice, and they were reacted. After 10 min, 200 µl of toluene was added, and the mixture was stirred for 6 hours at room temperature. The reaction mixture was dissolved in 5 ml of ethyl acetate, and the solution was washed well with an aqueous saturated sodium chloride solution. The organic layer was dried over sodium sulfate, concentrated, and the residue was purified by preparative thin-layer chromatography, to obtain 21 mg of Ia as an oil. Yield: 78%. MS m/z: 365.0890 ($M^+$); calculated for $C_{19}H_{21}Cl_2NO_3$=365.0949. The $^1$H-NMR spectrum corresponded to the expected structure.

SYNTHETIC EXAMPLE 2

(Synthesis of (±)-4-bis(2-chloroethyl)aminophenyl 2-methoxy-2-phenylacetate (Ib))

Fifty-two mg of (±)-2-methoxy-2-phenylacetic acid was dissolved in 0.6 ml of tetrahydrofuran, and then 60 mg of carbonyldiimidazole was added into the solution under cooling with ice with stiring. After the stirring was continued for 10 min, a solution of 20 mg of p-hydroxyaniline mustard in 200 µl of tetrahydrofuran was added, and the mixture was stirred for 1 hour under cooling with ice, and then it was further stirred for 1 day at room temperature. The product was separated by preparative thin-layer chromatography (silica gel: $F_{254}$; developed with 5% EtOAc/benzene), to obtain 8 mg of Ib as an oil. Yield: 28%. MS m/z: 381.0740 ($M^+$); calculated for $C_{19}H_{21}Cl_2NO_3$=381.0898. The $^1$H-NMR spectrum corresponded to the expected structure.

SYNTHETIC EXAMPLE 3

(Synthesis of (±)-4-bis(2-chloroethyl)aminophenyl 2-trifluoroacetamido-3-phenylpropionate (Ic))

The synthesis procedure of Ib was repeated, except that 80 mg of (±)-N-trifluoroacetylphenylalanine was used, thereby obtaining 9 mg of Ic as a syrup. Yield: 26%. Part of this product was dissolved in ethanol and was allowed to stand at a low temperature, resulting in the formation of fine needle crystals (having a melting point of 75° to 78° C. MS m/z: 476.0941 ($M^+$); calculated for $C_{21}H_{21}C_2F_3N_2O_3$= 476.0881. The $^1$H-NMR spectrum corresponded to the expected structure.

SYNTHETIC EXAMPLE 4

(Synthesis of Optically Active Substances of 4-bis(2-chloroethyl)aminophenyl 2-methoxy-2-phenylacetate (Ib)

The same reaction as that in Synthetic Example 2 was carried out, except that (R)-(−)-2-methoxy-2-phenylacetic acid, manufactured by Aldrich Chemical Co., Inc., was used, thereby obtaining levo-rotatory Ib as an oil, in a yield of 44%. $[\alpha]_D^{28}$ −60.8° (c=1.9, ethanol). The same reaction and treatment as above were carried out, except that (S)-(+)-2-methoxy-2-phenylacetic acid, manufactured by Aldrich Chemical Co., Inc., was used, thereby obtaining dextro-rotatory Ib as an oil, in a yield of 51%. $[\alpha]_D^{28}$ +82.7° (c=1.7, ethanol). The Rf values of these optically active substances by thin-layer chromatography corresponded to that of the above-mentioned racemic modification of Ib.

SYNTHETIC EXAMPLE 5

(Synthesis of Optically Active Substances of 4-bis(2-chloroethyl)aminophenyl 2-trifluoroacetamido-3-phenylpropionate (Ic)

The same reaction as that in Synthetic Example 3 was carried out, except that (S)-(+)-N-trifluoroacetylphenylalanine prepared from L-phenylalanine was used, thereby obtaining levo-rotatory (S)-(−)-Ic as an oil, in a yield of 61%. $[\alpha]_D^{28}$ −9.7° (c=2.5, ethanol). The same reaction and treatment as above were carried out, except that (R)-(−)-N-trifluoroacetylphenylalanine prepared from D-phenylalanine was used, thereby obtaining dextro-rotatory (R)-(+)-Ic as an oil, in a yield of 65%. $[\alpha]_D^{28}$ +10.3° (c=2.6, ethanol). The Rf values of these optically active substances by thin-layer chromatography corresponded to that of the above-mentioned racemic modification of Ic.

SYNTHETIC EXAMPLE 6

(Synthesis of 5'-(RS)-(2-phenylpropionyl)-5-fluorouridine (IIa))

Twenty-five mg of 2,'3'-isopropylidene-5-fluorouridine and 80 mg of (±)-2-phenylpropionic acid were coupled in 1.8 ml of tetrahydrofuran by using 75 mg of carbonyldiimidazole in the same way as in Synthetic Example 2. After the obtained product (39 mg; crystallized from methanol; melting point: 169° to 170° C.) was separated by preparative thin-layer chromatography (silica gel: $F_{254}$; developed with 50% EtOAc/benzene), the product was dissolved in a mixed liquid of 0.2 ml of methanol and 0.8 ml of trifluoroacetic acid, and it was allowed to stand for 30 minutes at room temperature, thereby decomposing the isopropylidene group. The reaction liquid was concentrated under reduced pressure, and the residue was purified by preparative thin-layer chromatography (silica gel: $F_{254}$; developed with 2% MeOH/EtOAc), to obtain 26 mg of fine needle crystals of IIa. Yield: 80%; melting point: 133° to 134° C.; MS m/z: 394.1048 ($M^+$); calculated for $C_{18}H_{19}FN_2O_7$=394.1176. The $^1$H-NMR spectrum corresponded to the expected structure.

SYNTHETIC EXAMPLE 7

(Synthesis of 5'-(RS)-(2-methoxy-2-phenylacetyl)-5-fluorouridine

The same reaction and treatment as those of the above Synthetic Example were repeated, except that 25 mg of 2',3'-isopropylidene-5-fluorouridine and 80 mg of (±)-2-methoxy-2-phenylacetic acid were used, thereby obtaining 33 mg of a syrup of IIb. Yield: 97%. MS m/z: 410.1154 (M+); calculated for $C_{18}H_{19}FN_2O_8$=410.1125. The $^1$H-NMR spectrum corresponded to the expected structure.

SYNTHETIC EXAMPLE 8

(Synthesis of (5'-(RS)-(2-trifluoroacetamido-3-phenylpropionyl)-5-fluorouridine (IIc))

The same reaction and treatment as those of Synthetic Example 4 were repeated, except that 70 mg of (±)-N-trifluoroacetylphenylalanine was used, thereby obtaining 51 mg of a syrup of IIc. Yield: 61%. MS m/z: 505.1002 (M+); calculated for $C_{20}H_{19}F_4N_3O_8$=505.1108. The $^1$H-NMR spectrum corresponded to the expected spectrum.

EXAMPLE 1

The thus synthesized esters for anticancer agent were respectively incubated with cancer cells, rat whole blood, normal rat tissue homogenate, or human whole blood, and for each sample the hydrolyzed rate, and the absolute configuration and the optical purity of the produced carboxylic acid, were examined. Each of the reaction mixtures was prepared by dissolving 1 mg of the ester in 10 μl of ethanol, and by mixing with it, 90 μl of a 0.1M phosphoric acid buffer (having a pH of 7.5), plus one of the following: 100 μl of a cell suspension, or 20 or 30 μl of whole blood, or 50 μl of tissue homogenate. The cancer cells were cultured by a method described in the literature (T. Okada et al., Inorg. Chem. Acta. 178, 13 (1990) and a catalogue of American Type Culture Collection), and the cells were washed well with the above phosphoric acid buffer that had been cooled with ice. The cells numbers in 100 μl of the cell suspension used in the reaction were as follows: rat liver cancer cells Anr4=$7 \times 10^6$; rat pancreas cancer cells ARIP=$8 \times 10^6$; rat sarcoma cells XC=$5 \times 10^6$; human histiocytic leukemia cells U937=$1 \times 10^7$; human pancreas cancer cells MIA PaCa-2=$8 \times 10^6$; and human intestinum crassum cancer cells Colo 320=$1 \times 10^7$. Fifty μl of the tissue homogenate corresponded to 20 mg of wet tissue.

Each of these reaction mixtures was stirred for 12 hours at 30° C. by a magnetic stirrer; then 1.5 μl of 2N HCl was added, to bring the pH to about 2.5, and extraction with 1 ml of ethyl acetate in the presence of a saturated sodium chloride was carried out twice. The ethyl acetate layers of each sample were combined, the volume was adjusted to precisely 2 ml, and it was divided into 1.7 ml and 0.3 ml. The former was concentrated under reduced pressure, and the contained produced carboxylic acid was isolated by thin-layer preparative chromatography. A solution of diazomethane in ether was added to it, to methylate it, and the absolute configuration and the optical purity of the methylated product were determined by high-performance liquid chromatography using a chiral column. The latter 0.3 ml was directly methylated, and then it was concentrated and adjusted to 0.3 ml again, and the methyl ester of the contained produced carboxylic acid was determined quantitatively by gas chromatography, from which the hydrolyzed rate was determined. The column used in the high-performance liquid chromatography was a Chiralcell OJ or OD column (trade name; 4.6×250 mm) manufactured by Daicel; the elution was carried out by using a 10% 2-propanol/hexane mixture; and the flow velocity was 1 or 0.75 ml/min. The column used in the gas chromatography was a capillary column of OV-1 (0.25 mm×25 m), and the analysis temperature was 120° to 180° C. The methyl ester used as a standard sample in the chromatography was prepared from a commercially available optically active carboxylic acid and racemic carboxylic acid. The results are summarized in Table 1.

TABLE 1

Stereoselectivity of Hydrolysis of the Anticancer Agent Esters with Cancer Cells and Tissue of Organisms

| | Cancer Cells of Rat Origin | | | Cancer Cells of Humans Origin | | | Rat Normal Tissue | | | | Human |
|---|---|---|---|---|---|---|---|---|---|---|---|
| | Anr4 | ARIP | XC | U937 | MIA PaCa-2 | Colo320 | Whole blood | Liver | Pancreas | Muscle | Whole Blood |
| Ia | R 68.9 (20.9) | R 42.8 (10.2) | R 18.6 (6.3) | R 72.3 (5.2) | R 87.1 (6.0) | R 68.9 (3.0) | R 9.4 (5.8) | R 15.7 (15.1) | R 1.0 (35.0) | S 1.8 (7.8) | R 9.1 (2.4) |
| Ib | R 91.3 (14.0) | R 26.8 (55.2) | R 69.9 (23.9) | NT | NT | NT | R 20.4 (55.2) | R 33.2 (29.1) | S 8.4 (66.7) | R 46.0 (56.2) | NT |
| Ic | R 94.9 (0.6) | R 83.0 (14.6) | R 77.9 (10.6) | R >99 (9.6) | S 2.6 (7.2) | R 35.9 (2.4) | R 18.3 (18.2) | R 93.2 (16.4) | R >99 (24.8) | R 72.4 (14.9) | S 23.7 (8.0) |
| IIa | R 81.6 (26.3) | R 91.3 (25.2) | R 82.1 (16.8) | R 38.2 (NT) | NT | NT | R 53.7 (6.3) | R 85.6 (17.9) | S 36.9 (15.8) | R 61.7 (4.7) | R 12.5 (5.3) |
| IIb | R 81.1 (23.7) | R 84.1 (27.7) | R 81.5 (23.0) | NT | NT | NT | S 55.0 (14.8) | R 6.0 (47.9) | R 42.5 (47.9) | S 18.5 (17.8) | NT |
| IIc | R 98.4 (7.8) | R >99 (1.9) | R >99 (3.4) | R 57.8 (12.6) | R 19.0 (20.6) | R 64.6 (13.8) | S 41.8 (16.3) | R >99 (6.6) | R >99 (26.8) | R 87.8 (5.8) | S 66.9 (36.1) |

Note:
1) R and S in the Table indicate which acyl group having the particular absolute configuration is preferentially hydrolyzed, and the numerical value after it indicates the optical activity of the carboxylic acid produced by the hydrolysis, in terms of the enantiomer excess (% e.e.). The numerical value in parenthesis is the hydrolyzed rate (%).
2) NT means that no experiment was done.

EXAMPLE 2

The anticancer effect of levo-rotatory or dextro-rotatory 4-bis(2-chloroethyl)aminophenyl 2-methoxy-2-phenylacetate (Ib) on rat liver cancer cells Anr4 was tested. Anr4 cells were suspended, in an amount of cells number of $1\times10^6$ per 1 ml, in William's E medium containing 10% of fetal bovine serum, and 0.1 ml of the suspension was distributed to each well of a 24-well multiplate. Further, 1.385 ml of the above medium was added to each well. They were cultured for 4 hours at 37° C. in a $CO_2$ incubator, and then 15 μl of pure ethanol or an ethanol solution containing (R)-(−)-Ib or (S)-(+)-Ib obtained in Synthetic Example 4, having a concentration of 10 mM, 1 mM, 0.1 mM, 0.01 mM, or 0.001 mM, was added to the medium in each well, and they were mixed well.

After they were cultured for 6 hours in the above incubator, the medium was removed by suction, and 1.5 ml of fresh medium was added. After culturing was continued for 42 hours, the number of cells in each well was counted by a Coulter counter. The results, in terms of % for the value of the control (the well added pure ethanol), were 9%, 12%, 16%, 55%, and 95% for the concentrations of 100 μM, 10 μM, 1 μM, 0.1 μM, and 0.01 μM of (R)-(−)-Ib in the medium, respectively. For the concentrations of 100 μM, 10 μM, 1 μM, 0.1 μM, and 0.01 μM of (S)-(+)-Ib in the medium, the results were 9%, 18%, 30%, 83%, and 95%, respectively. These results show that, at concentrations of 1 μM to 0.1 μM, the levo-rotatory (R)-(−)-Ib suppressed the multiplication of Anr4 cells more strongly than dextro-rotatory (S)-(+)-Ib did. This is in conformity with the above finding, that Anr4 showed preferential stereoselectivity for the R enantiomer in hydrolysis of (±)-Ib.

EXAMPLE 3

The anticancer effect of the optically active substances of Ic obtained in Synthetic Example 5 on Anr4 cells was tested in the same way as in Example 2. As a result, at 10 μM, (R)-(+)-Ic suppressed the multiplication of Anr4 cells to 14% of the control, and (S)-(−)-Ic suppressed the multiplication of Anr4 cells to 25% of the control. These findings show that (R)-(+)-Ic has a stronger cell multiplication-suppressing effect than (S)-(−)-Ic, and this is in conformity with the above finding that, in the hydrolysis of (±)-Ic, Anr4 showed preferential stereoselectivity for the R enantiomer.

Having described our invention as related to the present embodiments, it is our intention that the invention not be limited by any of the details of the description, unless otherwise specified, but rather be construed broadly within its spirit and scope as set out in the accompanying claims.

What we claim is:

1. An ester compound having a structure represented by the formula (I):

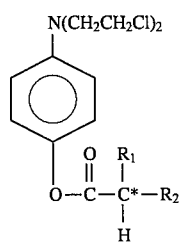

formula (I)

wherein $R_1$ represents a methyl group, a methoxy group, or a trifluoroacetamido group; $R_2$ represents a phenyl group or a phenylmethyl group; and the absolute configuration of the asymmetric center marked with an asterisk is R.

2. The ester compound as claimed in claim 1, wherein $R_1$ is a methyl group and $R_2$ is a phenyl group; $R_1$ is a methoxy group and $R_2$ is a phenyl group; or $R_1$ is a trifluoroacetamido group and $R_2$ is a phenylmethyl group.

3. A method of producing an ester of p-hydroxyaniline mustard that is improved in pharmacokinetics, comprising acylating the hydroxyl group in the p-position of a p-hydroxyaniline mustard with an acyl group represented by the formula (III), wherein the absolute configuration of the asymmetric center marked with an asterisk is R:

formula (III)

wherein $R_1$ represents a methyl group or a trifluoroacetamido group; $R_2$ represents a phenyl group or a phenylmethyl group; and the absolute configuration of the asymmetric center marked with an asterisk is R.

4. The method of producing an ester as claimed in claim 3, wherein the acyl group represented by the formula (III) is represented by the formula (IIIa), (IIIb), or (IIIc):

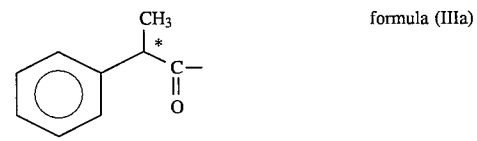

formula (IIIa)

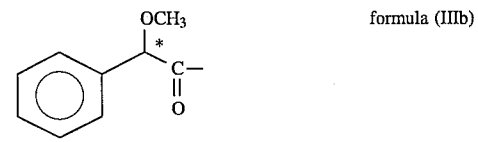

formula (IIIb)

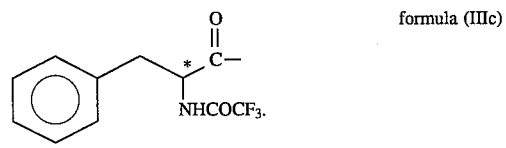

formula (IIIc)

5. The method of producing an ester as claimed in claim 3, comprising activating the (R)-carboxylic acid corresponding to the acyl group represented by formula (III) by a known method; and coupling the (R)-carboxylic acid with p-hydroxyaniline mustard.

* * * * *